April 9, 1957 W. S. SAWLE, JR Plant Pat. 1,587
APPLE TREE
Filed Nov. 27, 1953
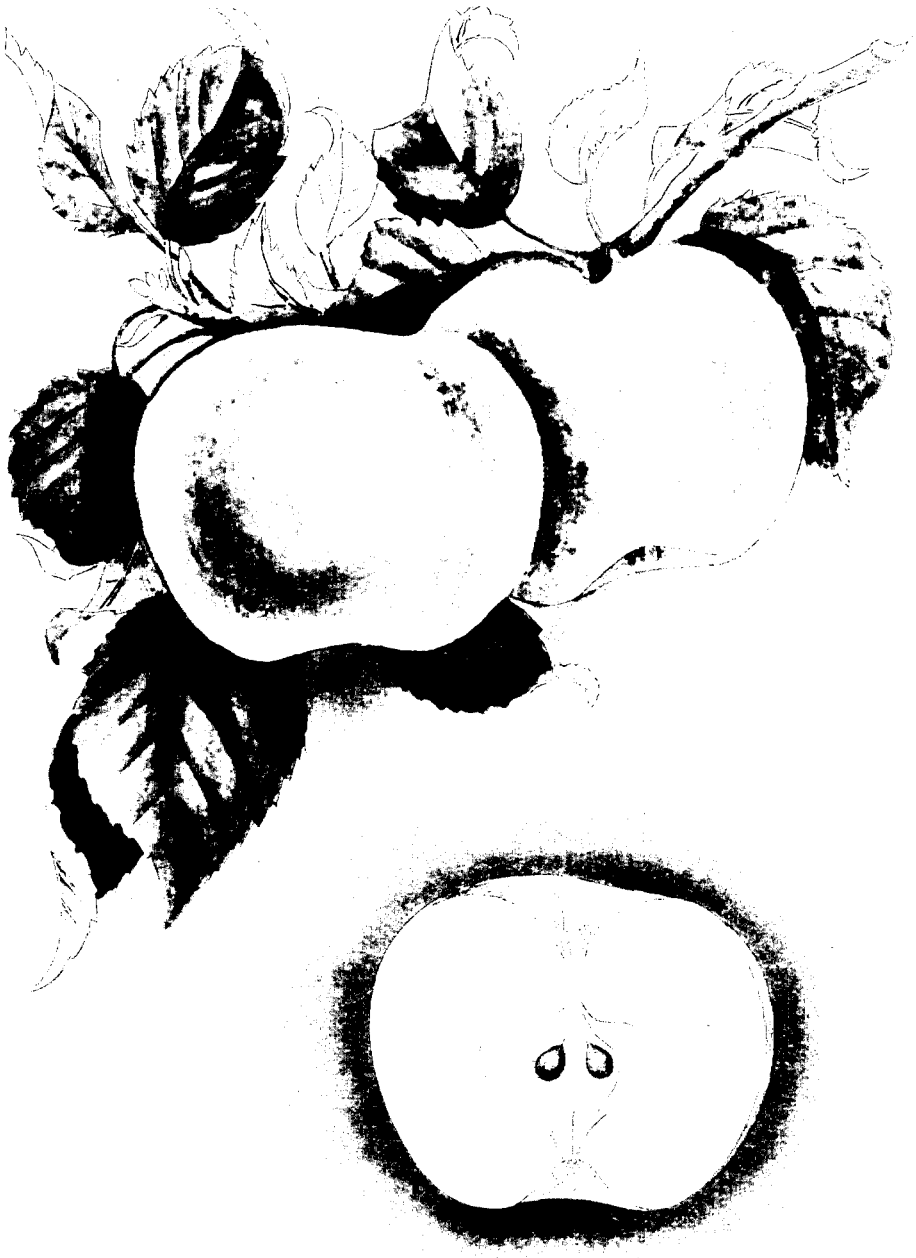
WITNESS
Addison E. Avery
INVENTOR
William S. Sawle, Jr.,
by: Gehr & Leonard,
his ATTYS.

United States Patent Office

Plant Pat. 1,587

Patented Apr. 9, 1957

1,587

APPLE TREE

William Stephen Sawle, Jr., Kenilworth, Ill.

Application November 27, 1953, Serial No. 394,913

1 Claim. (Cl. 47—62)

This invention relates to a new and distinct variety of apple tree.

The new variety is illustrated in the drawing, in which:

The upper one of the views illustrates a part of a branch of the new variety with the leaves and fruit thereon as they appear at maturity; and The lower one of the views illustrates half of one of the fruits cut in half axially so as to disclose the flesh, core and seeds.

Both views are full scale and represent specimens of average size.

The present variety is a chance seedling from an unknown variety. The seedling was discovered in Arena, Wisconsin, in the front yard of an inhabited dwelling in cultivated soil adjacent a rose bush about which the soil was customarily kept somewhat loose and is believed to have resulted from the seeds of the unknown variety having been inadvertently dropped at the growing site. The soil in which the seedling was found was in a state of cultivation at the time of discovery of the seedling and had been kept in a state of cultivation for an interval beginning at a date long prior to said discovery and continuing to a date subsequent to said discovery at which latter date the seedling had become an established and thriving plant.

There were no apple trees within close proximity to the growing site and it does not appear likely that the tree could have resulted from the seeds of any of the apple trees known to have existed in the vicinity.

Shoots of the seedling appeared above the foliage of the rose bush and the seedling was protected and permitted to remain growing until it matured into a fruit producing tree.

I had observed the tree and its fruit and considered it unusual and planned to reproduce it asexually. I arranged to obtain buds for the asexual reproduction, but when I arrived at the site at which the tree had been growing, I found that the tree had been blown down and hauled away several days before I arrived. I managed to find the remnants of the tree where they had been dumped and observed that the sap had not yet started to run. Consequently, I took from the tree remnants a branch with some sound looking buds thereon. Of these buds, I grafted about 15 to apple roots, by budding one bud to each root. I obtained the roots from a nursery. These grafts grew successfully at Kenilworth, Illinois, but late in the summer of the same year I went away for about ten days and during this time, the weather became extremely dry and hot and all but three of the grafted trees died.

The three surviving trees I nurtured and protected from rodents and subsequently transplanted them at a second location in Kenilworth, Illinois. Later in December, 1951, when they were about 15 feet high, I removed them from the second location and transplanted them at their present location at 151 Sheridan Road, Kenilworth, Illinois, where in the spring of 1953 they bloomed profusely.

In August, 1953, they produced an abundance of ripened fruits which, so far as I can tell, are identical in all respects to those produced by the parent tree. The reproduced trees are now growing at my present address.

The asexually reproduced trees have grown successfully with the roots unprotected in latitude 42° North and at temperatures ranging from 110°, Fahrenheit, in summer to 30° below zero, Fahrenheit, in winter. The present specimens are growing and producing, unprotected both above and below ground, at about latitude 42° North.

The tree is a vigorous grower and does well in good quality loam soil with average drainage. It is relatively compact and symmetrical and lends itself well to shaping by pruning and the like. The present specimens, now nine years old and having been twice transplanted in different locations, have reached a height of about 15 feet with a spread of about 10 to 12 feet. The upper or exposed portion of the plant, likewise, has exceptional resistance to disease and low temperature when unprotected. Though never sprayed, it does not appear to have been adversely affected by any disease or insect pests and very few of the resultant fruits are wormy. It bears well in a sunny location. Since relatively small specimens bear abundantly and for a long seasonal period, the tree is particularly desirable for small building lots. The bearing period extends from the forepart of August until November in latitude 42° North on the shores of Lake Michigan.

A distinctive feature of the tree is the long ripening period of the fruit which period extends from about September 10th to November 1st. The apples never get so ripe that they fall from the tree. They have been known to hang on to the tree well into December. The first picking is about August 10th, at which time the apples are suitable for cooking. The last picking is about November 15th. The major portion of the fruit is ripened for picking about the middle of October. The branches are strong and adequate to support the abundance of fruit. The trunk of the tree is medium smooth, and the branches are smooth and greenish grey.

The fruits are of average size with strong stems which adhere and support them after ripening for a period somewhat longer than average. They are quite uniform in size. The apples are somewhat ovate or orbicular, having an axial diameter of from 2¼ inches to 2½ inches and a transverse diameter of 3 inches. They are truncated at the apex and somewhat truncated at the base. The cavity is symmetrical, abrupt at the base, acute and undulate. It is inconspicuously pubescent toward the apex. It is about 7/16 of an inch in depth and about ⅔ of an inch in the breadth. In color, it is a green comparable Plate 62/1, page 62, volume 1 of the Horticultural Color Chart.

The basin is symmetrical, abrupt and wide flaring at the base, undulate and pubescent. The depth is about 3/16 inch and the breadth ⅝ inch. There are no distinctive markings.

The stems average, in length, about ¾ inch and in breadth about ⅛ inch. They are pubescent and speckled.

The calyx is open, and the segments are persistent. It is broadly lanceolate, separated at the base, and reflexed from the base at the apex. The inner and outer surfaces are pubescent.

The eye is open and large.

The skin is medium thin and is firm and smooth. It has many conspicuous small circular dots which are colored Cyprus Green, comparable to the Horticultural Color Chart, Plate 59/3, page 59, vol. 1. The dots are fairly uniformly distributed over the surface. The ground color of the skin is Geranium Lake, comparable to the Horticultural Color Chart, Plate 20/1, page 20, vol. 1 shading into a color comparable to Plate 20/2. The skin is free from bloom. There is not scarfskin. The general color effect is red with yellow and green shading.

The fruit has excellent resistance to decay and deterioration after ripening. Specimens have been kept in an unheated basement from the harvest time in the fall until the month of May of the following year. The specimens so stored remained in good condition, the flesh at the end of the storage period remaining juicy and crisp and the flavor being exceedingly well preserved.

The flesh of the fruit is slow to discolor and brown when cut and exposed to the air, thus making the fruit particularly suitable for salads. In fact, due to its consistency and flavor the fruit appears to be well adapted not only for salads but for sauces, pies, ciders and for baking. At the same time, due to its very fine flavor, texture and crispness when raw, it is very desirable as an eating apple.

The flesh is generally very suitable for desserts and various culinary purposes. The taste is sweet, even before ripening. The flesh is very juicy and tangy when ripe and never becomes soft and mealy.

The flesh of the fruit has a slightly off-white cast comparable to Maerz and Paul Plate 9–A to C–1. The seeds are of a relatively light burnt umber color, comparable to Maerz and Paul Plate 15–A–12, merging in darker areas with a Brazil brown comparable to Maerz and Paul Plate 8–L–8.

The outer surface of the fruit near the stem and upper part and near the base and lower part is of a light yellowish green, comparable to Maerz and Paul Plate 17–L–5, this color merging upon recession from the stem and along the upper and lower portions of the sides, to a buff or orange-yellow, comparable to Maerz and Paul Plate 11–K–7. The major portion of the surface, especially the part remote from the ends of the fruit, is red and ranges from a light red with a slightly yellowish cast, comparable to Maerz and Paul Plate 3–K–9, to a deeper and darker red, comparable to Maerz and Paul Plate 4–L–6, with which it merges gradually. This deeper red and portions of the yellowish red and green are splotched with markings and patches of a reddish-brown comparable to Maerz and Paul Plate 7–L–6. The core of the apple is sessile. The bundle area is large and ovate. It is unsymmetrical, being acute at the base and opposite and alternate with the cell. The halves of the core are unequal. The bundles are inconspicuous, being a single whorl.

The color of the core is Chartreuse Green, comparable to Plate 663/3, page 90, vol. 1, of the Horticultural Color Chart.

The core lines are meeting and distinct in cross-section, though small.

The calyx tube is glabrous and cone-shaped. Its entire depth is 1⅛ inches. There are no styles.

The seeds number about five perfect seeds, and they are arranged two seeds per cell. The seeds average about 5/16 inch in length and about 3/16 inch in breadth. They are ovate, pointed at the base, and rounded at the apex. They are a Brussels Brown, comparable to Plate III, Color No. 15, Tone of the Y–O Ridgway Chart.

The leaves on the upper surface are generally a light green, comparable to Maerz and Paul Plate 20–L–7, and on the underside are a green, comparable to Maerz and Paul Plate 19–D–4. The leaves average about 3 inches to 4 inches in length and about 1½ inches to 2 inches in width. They are ovate and acuminate with serrated margins. The color may further be designated as Spinach Green, comparable to Plate 0960/2, page 187, vol. 2, of the Horticultural Color Chart. The petioles are about ¾ of an inch to 1 inch long, and about 1/32 of an inch thick.

The flowers are large, and white with a pink tinge. They first bloom during a period from about April 25th to May 10th. They reach full bloom during a period of from about April 30th to May 15th, depending upon when they first bloom.

The plant generally is characterized by its extreme hardiness, its strong branches capable of supporting well the abundant fruit which it bears, its long seasonal bearing period, and its characteristic of retaining the fruit without dropping for longer periods than usual after ripening, and the abundance of its fruit.

However, its most important characteristic resides in the fruit itself which is characterized particularly by the exceedingly crisp, juicy texture and the tangy, sweet flavor of its flesh; its exceptional keeping qualities; and its fine cooking and eating qualities.

Having shown and described my new variety of apple plant and its mode of asexual reproduction, I claim:

The new and distinct variety of apple tree substantially as herein illustrated and described.

No references cited.